(12) United States Patent
Hanlon et al.

(10) Patent No.: US 8,579,887 B2
(45) Date of Patent: Nov. 12, 2013

(54) AXIALLY RECIPROCATING MICROSURGICAL INSTRUMENT WITH RADIALLY COMPRESSED ACTUATOR HANDLE

(75) Inventors: Matthew A. Hanlon, O'Fallon, MO (US); Richard Ormsby, O'Fallon, MO (US)

(73) Assignee: Synergetics USA, Inc., O'Fallon, MO (US)

( * ) Notice: Subject to any disclaimer, the term of this patent is extended or adjusted under 35 U.S.C. 154(b) by 140 days.

(21) Appl. No.: 12/942,460

(22) Filed: Nov. 9, 2010

(65) Prior Publication Data

US 2012/0116361 A1 May 10, 2012

(51) Int. Cl.
*A61B 17/00* (2006.01)

(52) U.S. Cl.
USPC .............................. 606/1; 606/205; 606/174

(58) Field of Classification Search
None
See application file for complete search history.

(56) References Cited

U.S. PATENT DOCUMENTS

| | | |
|---|---|---|
| 3,921,640 A | 11/1975 | Freeborn |
| 4,760,848 A | 8/1988 | Hasson |
| 5,211,652 A | 5/1993 | Derbyshire |
| 5,275,607 A | 1/1994 | Lo et al. |
| 5,290,302 A | 3/1994 | Pericic |
| 5,338,317 A | 8/1994 | Hasson et al. |
| 5,370,658 A | 12/1994 | Scheller et al. |
| 5,634,918 A | 6/1997 | Richards |
| 5,827,291 A | 10/1998 | Fucci et al. |
| 5,830,231 A | 11/1998 | Geiger |
| 5,893,873 A | 4/1999 | Rader et al. |
| 5,908,426 A | 6/1999 | Pierce |
| 5,928,263 A | 7/1999 | Hoogeboom |
| 5,984,865 A | 11/1999 | Farley et al. |
| 6,391,046 B1 | 5/2002 | Overaker et al. |
| 6,482,198 B1 | 11/2002 | Overaker et al. |
| 6,488,695 B1 * | 12/2002 | Hickingbotham ............ 606/206 |
| 6,855,126 B2 | 2/2005 | Flinchbaugh |
| 6,855,156 B2 | 2/2005 | Etter et al. |
| 2006/0004250 A1 * | 1/2006 | Parihar et al. .................. 600/37 |
| 2006/0089661 A1 | 4/2006 | Dodge et al. |
| 2007/0179475 A1 * | 8/2007 | Scheller ........................... 606/1 |
| 2007/0185512 A1 | 8/2007 | Kirchevel |
| 2007/0185514 A1 | 8/2007 | Kirchevel |

FOREIGN PATENT DOCUMENTS

| | | |
|---|---|---|
| DE | 3526821 | 5/1987 |
| GB | 2091624 | 8/1982 |

* cited by examiner

*Primary Examiner* — Sam Yao
*Assistant Examiner* — Scott T Luan
(74) *Attorney, Agent, or Firm* — Joseph M. Rolnicki; Evans & Dixon, LLC

(57) ABSTRACT

A microsurgical instrument has a pair of operative surgical surfaces that are moved relative to each other in shearing or grasping procedures performed by the instrument. The instrument has a handle containing an elongate center rod with a ring mounted for reciprocating movement on the rod. A tube is secured to the ring and a shaft extends through the tube and is secured to the rod. The handle also includes a plurality of resilient arms that extend along the length of the rod and engage against a sliding surface of the ring on the rod. The plurality of actuator arms are alternatively manually compressed radially inwardly by the surgeon's hand and released by the surgeon's hand to allow the arms to flex radially inwardly and outwardly. The inward and outward movement of the plurality of arms reciprocates the ring on the handle rod and causes the tube and shaft to move axially relative to each other.

13 Claims, 5 Drawing Sheets

US 8,579,887 B2

AXIALLY RECIPROCATING MICROSURGICAL INSTRUMENT WITH RADIALLY COMPRESSED ACTUATOR HANDLE

BACKGROUND OF THE INVENTION

1. Field of the Invention

The present invention pertains to a microsurgical instrument having a pair of operative surgical surfaces that are moved relative to each other in shearing or grasping procedures performed by the instrument, where the surgical instrument has an actuator handle with actuators that are radially compressed by the fingers of an operator's hand in controlling the movement of the operative surgical surfaces.

2. Description of the Related Art

Microsurgical instruments are those types of surgical instruments employed in performing surgical operations on extremely small and extremely delicate parts of the human anatomy, for example the tissues inside the human eye. There are many different types of microsurgical instruments. The more complex in construction are microsurgical instruments that have at least one pair of operative surgical surfaces that move relative to each other when using the instrument. By operative surgical surfaces what is meant is, for example, the opposed shearing surfaces of a scissors that have shearing edges that move across each other in a shearing operation performed by the instrument, or the opposed grasping surfaces of a forceps that move toward and away from each other in a grasping operation performed by the instrument. In microsurgical instruments of this type, the scale of the instrument must be as small as possible so that the introduction of the instrument to the surgical site is minimally invasive.

A typical microsurgical instrument is comprised of a manual handle that is similar in size and shape to a pen or pencil. This enables the instrument to be easily manipulated by the fingers on one hand of a surgeon. An example of this type of instrument is disclosed in U.S. Pat. No. 5,370,658, assigned to the assignee of the present invention and incorporated herein by reference.

Microsurgical instrument tips of the type disclosed in the above-referenced patent often comprise a hollow, narrow tube projecting from the instrument handle. A narrow fiber or shaft is received in the tube and the shaft and tube are caused to reciprocate relative to each other in response to manual manipulation of some type of actuator on the instrument handle. The relative movement between the shaft and tube operates the surgical instrument formed at the distal ends of the shaft and tube. Where the surgical instrument is a forceps, the opposed jaws of the forceps are formed at the shaft distal end and moving the tube over the shaft or retracting the shaft into the tube causes the forceps jaws to move toward each other. The reverse movements of the tube and shaft cause the jaws to separate from each other. Where the surgical instrument is a scissors, one of the shear surfaces is formed at the distal end of the shaft and the other shear surface is formed at the distal end of the tube. Moving the tube distal end toward the shaft distal end causes the shear surfaces and their shearing edges to move toward and across each other.

As stated earlier, for microsurgical applications, the surgical instruments discussed above must be manufactured in an extremely small scale. The small scale of the microsurgical instrument results in the operative microsurgical surfaces of the instrument moving relative to each other in response to the slightest movement of the instrument actuator by the fingers of the surgeon's hand.

SUMMARY OF THE INVENTION

It is therefore desirable that the microsurgical instrument have a handle that fits comfortably in the surgeon's hand and is easily rotated or otherwise moved in the surgeon's hand by slight manipulations of the fingers. It is also desirable that the actuator of the microsurgical instrument be easily and comfortably operated by the fingers of the surgeon's hand in any position of the instrument handle in the hand. It is also desirable that any resistance to the movement of the actuator of the surgical instrument be minimized.

The microsurgical instrument of the present invention is basically comprised of a surgical instrument head and a handle attached to the head. The surgical instrument head includes an elongate, narrow tube and a shaft or fiber that extends through the tube. The tube and shaft axially reciprocate relative to each other. The reciprocating movements of the tube and shaft produce movements of operative microsurgical surfaces of the instrument.

The microsurgical instrument also includes a rod having a length with opposite proximal and distal ends. The surgical instrument head is positioned at the distal end of the rod.

A ring is mounted on the rod for axially reciprocating movement between first and second positions of the ring along the rod length. The ring is movable toward the rod proximal end to the first position of the ring on the rod and the ring is movable toward the rod distal end to the second position of the ring on the rod. A conical surface is provided on the ring. The conical surface has a first hardness. In other embodiments of the instrument the ring surface could have a convex shape or a concave shape.

The instrument handle is provided on the rod proximal end. The handle has a plurality of arms that are circumferentially spaced around the rod. There are a plurality of axially extending slots between adjacent arms of the plurality of arms. The plurality of arms extend axially from the rod proximal end along the rod to free distal end surfaces of the arms. The free distal end surfaces of the arms have convex surfaces that are spaced radially outwardly from and surround the conical surface on the ring. Manually pressing the actuator arms radially inwardly with the fingertips causes the free distal ends of at least some of the arms to engage with and slide over the conical surface on the ring. This in turn causes the ring to move axially on the rod from the first position of the ring on the rod toward the second position of the ring on the rod. Releasing the manual force on the actuator arms allows the resilience of the arms to move the arms radially outwardly. The arms could also be spring biased to move radially outwardly. As the arms move outwardly a spring on the rod moves the ring from the second position of the ring on the rod toward the first position of the ring on the rod. This movement of the ring could also cause the ring conical surface to push the arms radially outwardly. The reciprocation of the ring on the rod produces relative axial reciprocating movements between the tube and shaft of the surgical instrument that in turn move the operative microsurgical surfaces of the instrument. The convex surfaces on the arm distal ends and the conical surface of the ring minimize the areas of contact between the arms and the ring and thereby minimize sliding friction between the distal end surfaces of the arms and the ring surface. In other embodiments the arm distal ends could each have a point that contacts the conical surface of the ring or a roller bearing or some other equivalent means of reducing the friction between the arm and the ring conical surface. The circumferential positioning of the arms around the ring enables the arms to be manually moved in any rotated position of the instrument in the surgeon's hands.

In addition, in an embodiment of the instrument, the surface on the ring is constructed of a material having a hardness that is greater than the hardness of the surfaces of the arms engaging the ring. The harder ring surface resists wear to the surface due to repeated radially sliding movements of the surfaces on the arms over the surface on the ring. Employing a stainless steel surface or other equivalent low friction surface on the ring further reduces friction between the surface on the ring and the surfaces on the actuator arms.

Still further, in an embodiment, the exterior surface of each of the actuator arms is configured in a manner that avoids any potential pinching of the surgeon's fingers between adjacent arms as the arms are moved radially toward each other by the surgeon's fingers compressing the arms.

Further features and advantages of the present invention, as well as the structure and operation of the present invention, are described in detail below with reference to the accompanying drawings.

BRIEF DESCRIPTION OF THE DRAWINGS

The accompanying drawings, which are incorporated in and form a part of the specification, illustrate the present invention and together with the description, serve to explain the principles of the invention.

DETAILED DESCRIPTION OF THE PREFERRED EMBODIMENT

The microsurgical instrument of the present invention is operable to axially reciprocate a tube and shaft of a surgical instrument similar to the microsurgical instruments disclosed in U.S. Pat. No. 5,370,658 which is assigned to the assignee of this application and is incorporated herein by reference. In surgical instruments of this type a narrow, cylindrical shaft or fiber extends through a narrow tube and the shaft and tube are reciprocated relative to each other to produce relative movement between the operative microsurgical surfaces of the instrument. The shaft can move in reciprocating movements relative to a stationary tube, or the tube can move in reciprocating movements relative to a stationary shaft. As described in the above-referenced patent, those operative microsurgical surfaces can be the surfaces of a microsurgical instrument such as a scissors or forceps.

Figure 1:
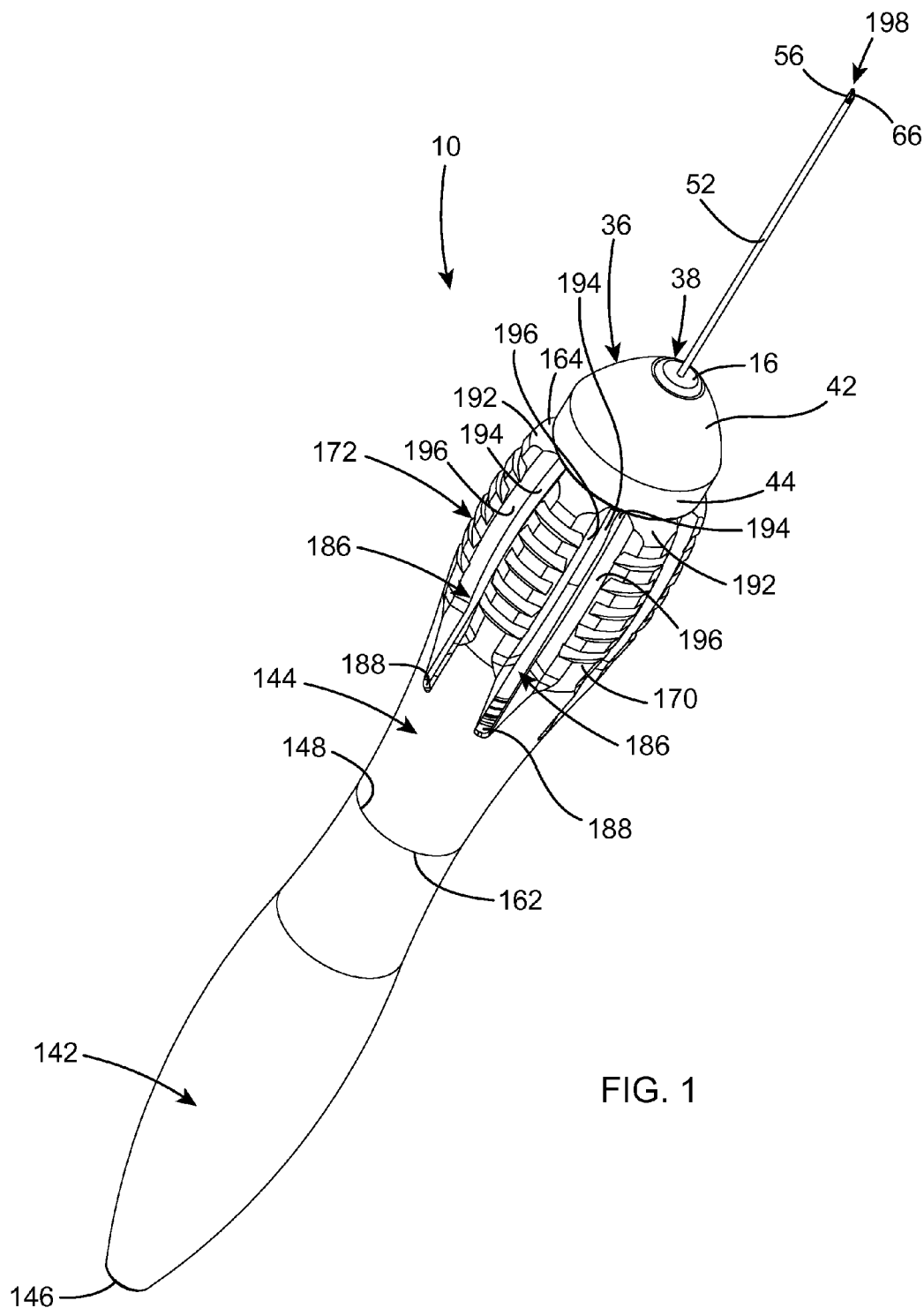
FIG. 1 is a front perspective view of the microsurgical instrument of the invention.
Figure 2:
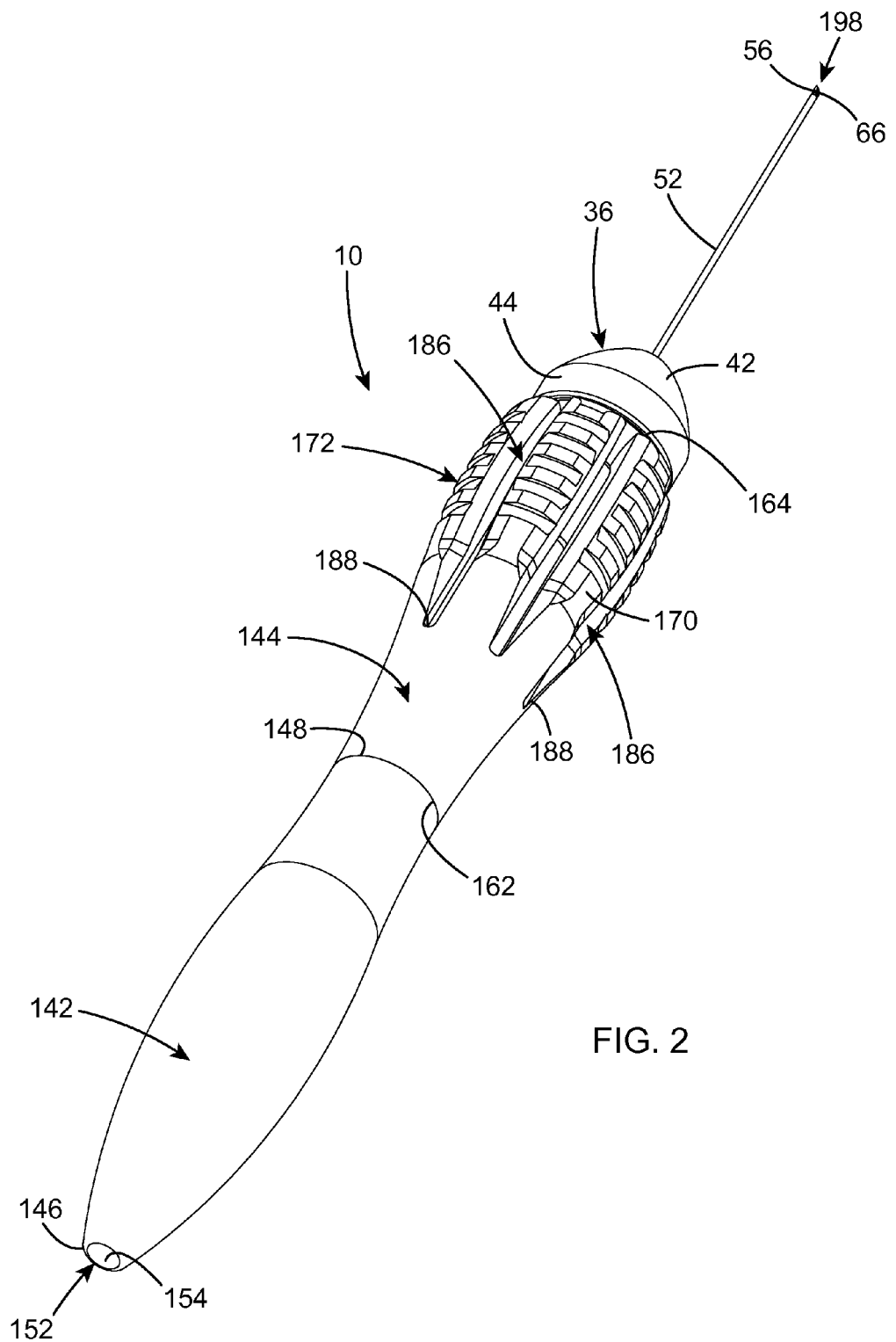
FIG. 2 is a rear perspective view of the microsurgical instrument of the invention.
Figure 3:
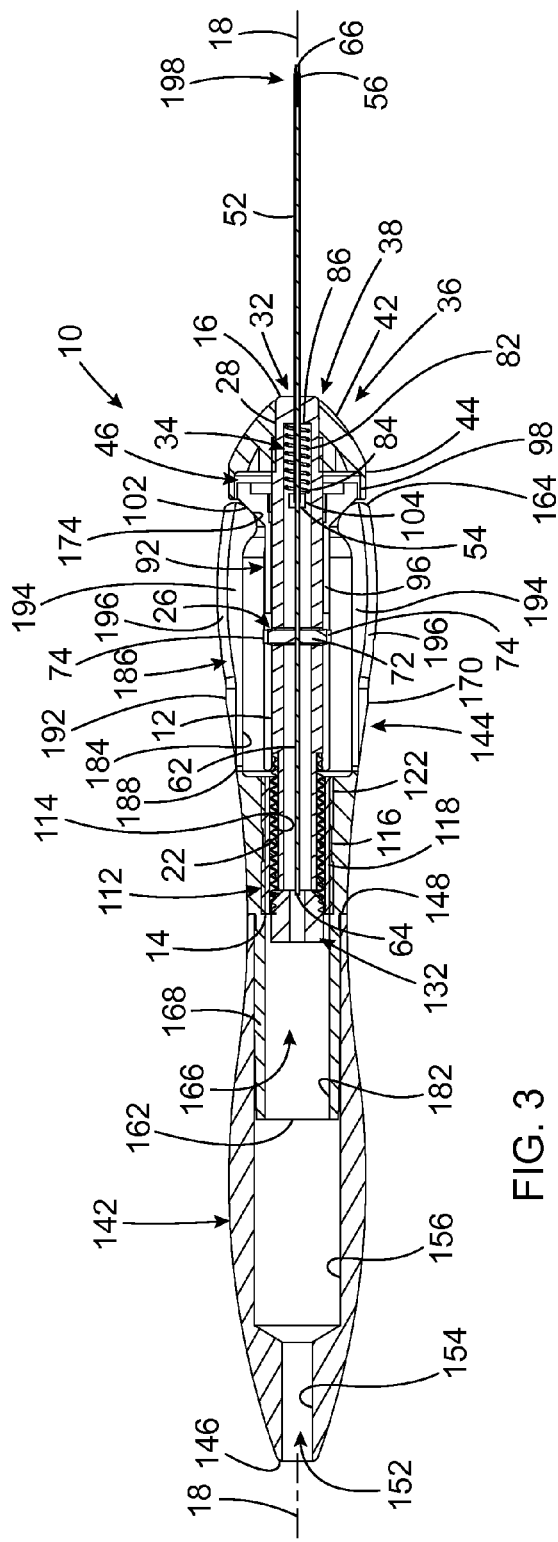
FIG. 3 is a cross-section side view of the microsurgical instrument of the invention.
Figure 4:
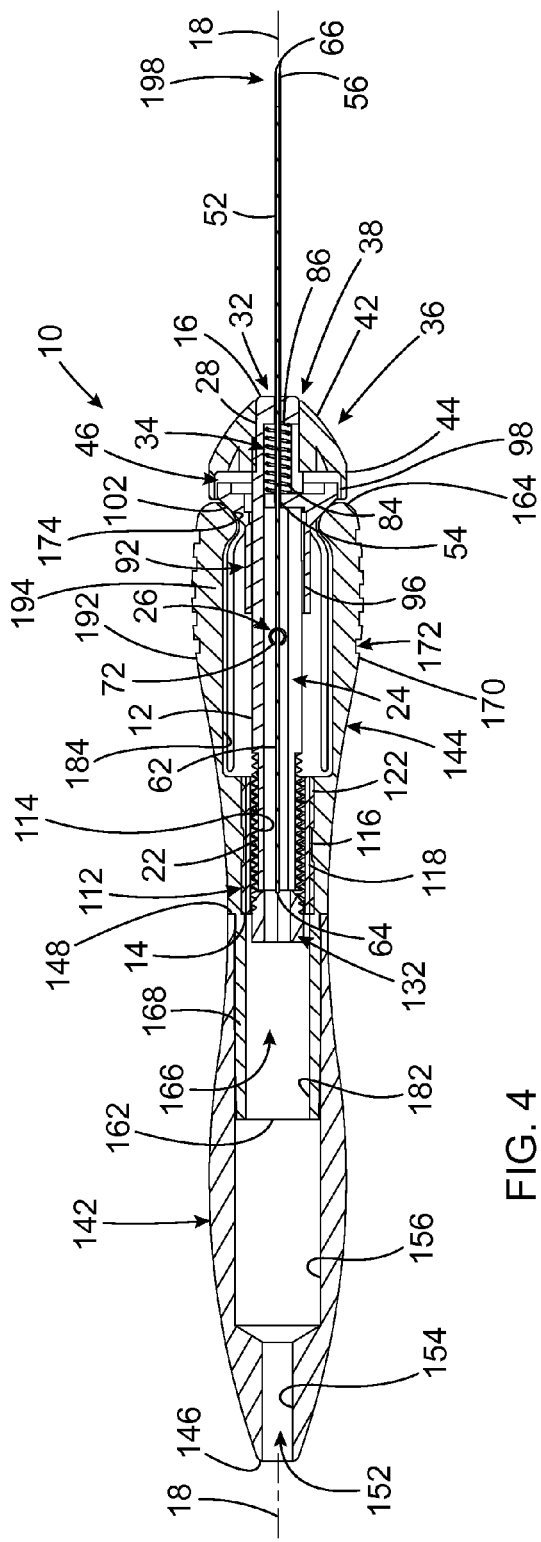
FIG. 4 is a cross-section side view of the microsurgical instrument rotated 90 degrees from the position of the instrument shown in FIG. 3.
Figure 5:
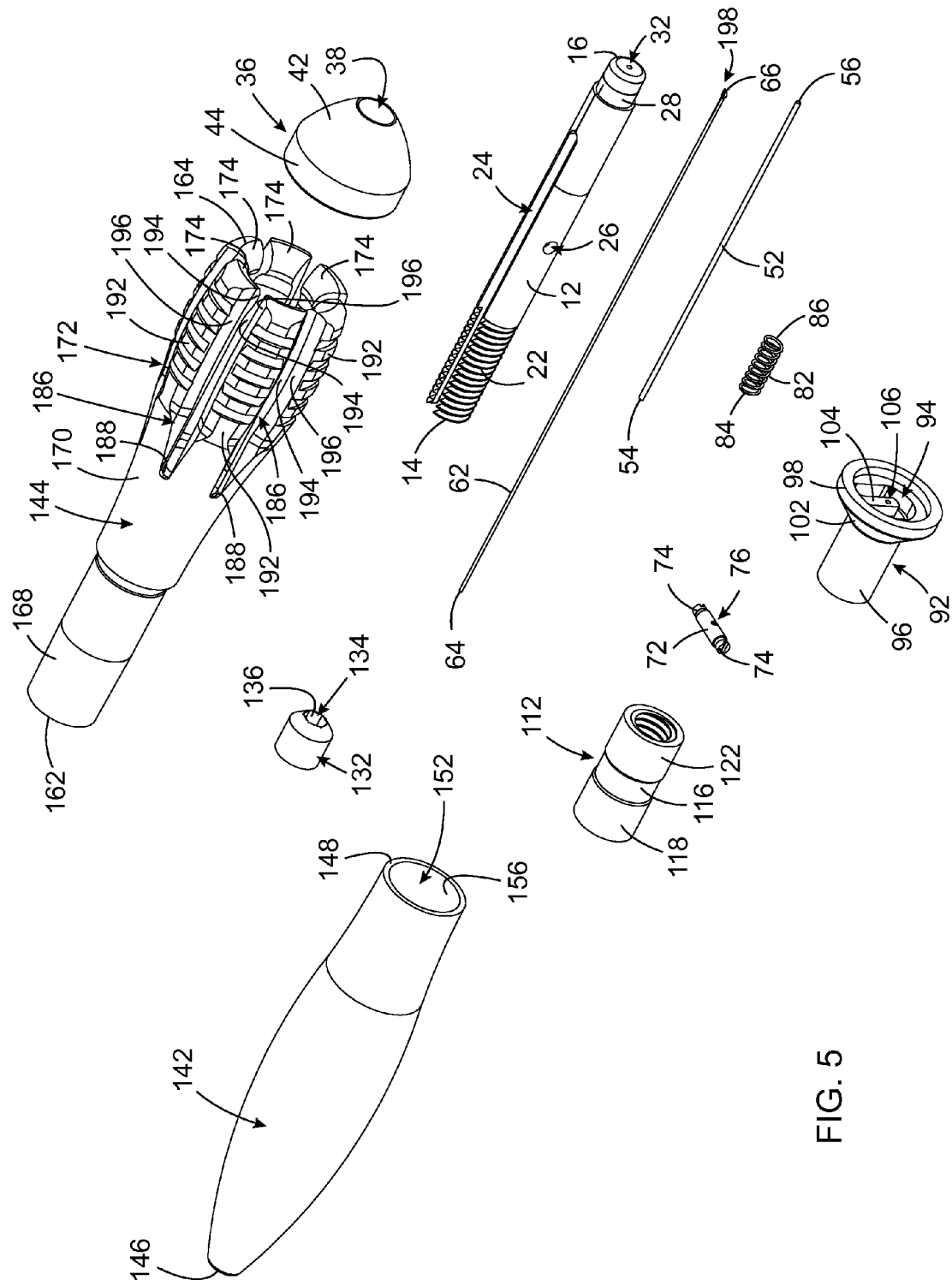
FIG. 5 is an exploded view of the component parts of the microsurgical instrument.
Figure 6:
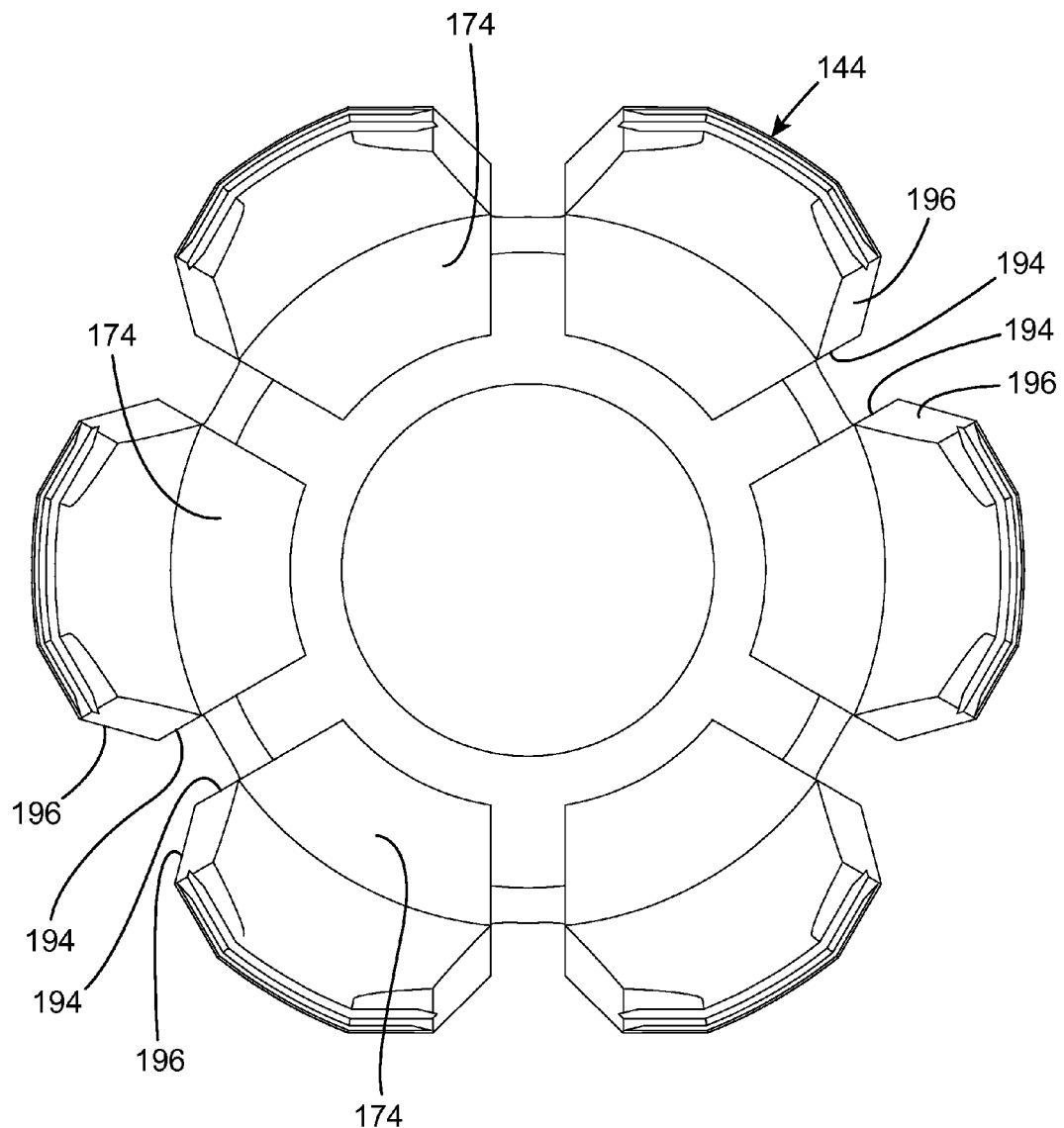
FIG. 6 is a front view of the distal end of the arms.

The microsurgical instrument 10 of the present invention is shown in a front perspective view in FIG. 1 and a rear perspective in FIG. 2. The component parts of the instrument 10 are shown in an exploded view in FIG. 5. In the preferred embodiment of the invention, all of the component parts of the instrument 10 to be described are constructed of a material that is capable of being sterilized, for example stainless steel and alloys of titanium or aluminum. However, it should be understood that the preferences set forth herein are not intended to be limiting and the instrument of the invention may be constructed from a variety of materials suitable for the purposes herein described.

The base of the microsurgical instrument 10 is an elongate cylindrical rod 12. The rod 12 has opposite proximal 14 and distal 16 ends and a center axis 18 that defines mutually perpendicular axial and radial directions relative to the microsurgical instrument 10. External screw threading 22 is formed on the rod 12 adjacent the rod proximal end 14. As shown in the drawing figures, the screw threading 22 extends from the rod proximal end 14 over the exterior surface of the rod 12 toward the rod distal end 16, but ends well short of the rod distal end. An elongate slot 24 is formed radially halfway through the width of the rod. The slot 24 extends through the center of the rod 12 from the rod proximal end 14 toward the rod distal end 16, but ends short of the rod distal end. A pin hole 26 extends through the width of the rod 12 and intersects the slot 24. The pin hole 26 is oriented perpendicular to the slot 24 and is located at an intermediate position along the rod length. A portion of the rod exterior surface 28 adjacent the rod distal end 16 is necked down. This portion of the rod 28 has a smaller diameter and a smaller circumference than the remainder of the rod exterior surface. A small center bore 32 is formed in the rod at the rod distal end 16. The center bore 32 has a center axis that is coaxial with the rod center axis 18. The center bore 32 extends from the rod distal end 16 through the center of the rod and intersects the slot 24. As the center bore 32 approaches the slot 24, the interior diameter of the bore increases forming an enlarged portion 34 of the bore that intersects the slot 24.

An instrument head 36 is mounted on the rod distal end 16. The instrument head 36 has a cylindrical center bore 38 that receives the rod necked down portion 28 at the rod distal end 16. The instrument head center bore 38 is press fit on the rod necked down portion 28 in securing the head 36 to the rod 12. Other means of securing the head 36 to the rod 12 could also be employed, for example employing adhesives to secure the head 36 to the rod 12 or making the head 36 an integral part of the rod 12. The instrument head 36 has a bulbous, generally convex distal end surface 42 that faces toward the rod distal end 16. A cylindrical wall 44 projects axially from the periphery of the head distal end surface 42 toward the rod proximal end 14. The wall 44 forms a cylindrical cavity 46 in an opposite side of the instrument head 36 from the head distal end surface 42.

A straight, narrow elongate tube 52 extends through the rod center bore 32 and the instrument head center bore 38. The tube 52 has a narrow, elongate length with opposite proximal 54 and distal 56 ends and a center axis that is coaxial with the rod center axis 18. In the preferred embodiment of the invention, the tube 52 has a construction similar to that of a hypodermic needle. The tube 52 is received through the rod center bore 32 and the instrument head center bore 38 for axially reciprocating movements of the tube 52 relative to the rod 12 and the instrument head 36. As described earlier, the tube distal end 56 forms a part of an operative microsurgical instrument that is similar to those of the earlier-referenced U.S. Pat. No. 5,370,658.

A rigid, straight narrow shaft 62 extends through the center of the tube 52. The shaft 62 has an elongate length with opposite proximal 64 and distal 66 ends and a center axis that is coaxial with the rod center axis 18. The shaft distal end 66 projects a short distance from the tube distal end 56 and forms the second part of the operative microsurgical instrument similar to those of the earlier referenced U.S. patent. The elongate length of the shaft 62 extends well beyond the tube proximal end 54 and through the rod slot 24 to the shaft proximal end 64. In the preferred embodiment of the invention, the shaft 62 is straight and rigid such as a length of rigid wire. However, in alternate embodiments of the microsurgical instrument 10, the shaft 62 can have a different construction, for example the construction of an optic fiber employed as an illumination light source or a laser light source in the microsurgical instrument 10.

A cylindrical tubular pin 72 extends through the pin hole 26 of the rod 12. The pin 72 has an internally threaded center bore with a center axis (not shown) that is perpendicular to the rod center axis 18. A pair of screws 74 are screw threaded into the pin center bore in the opposite ends of the pin 72. A shaft hole 76 extends through the pin 72 and is oriented perpendicular to the center bore of the pin. The shaft 62 extends through the shaft hole 76. The pin screws 74 are tightened down in the pin center bore at the opposite ends of the pin 72 and engage the shaft 62 between the screws 74 thereby securing the shaft 62 to the pin 72. In this manner, the pin 72 secures the shaft 62 relative to the rod 12.

With the tube 52 being capable of axially reciprocating movements relative to the rod 12 and the instrument head 36 as described above, the tube 52 is also capable of axially reciprocating movements over the shaft 62 secured to the rod. However, as described in the earlier referenced U.S. patent, the tube 52 could be secured to the rod 12 and the shaft 62 could be capable of axially reciprocating movements relative to the rod 12, the instrument head 36 and the tube 52.

A coil spring 82 is received in the enlarged portion 34 of the rod center bore. The coil spring 82 surrounds the tube 52 and the shaft 62 extending through the tube. The spring 82 has a distal end 84 that engages against an interior surface of the rod 12 at the bottom of the enlarged portion of the rod center bore 34. The opposite proximal end 86 of the spring 82 is positioned in a part of the enlarged portion 34 of the rod center bore 32 that intersects the rod slot 24.

A ring 92 is mounted on the rod 12 for axially reciprocating sliding movement of the ring 92 over the rod 12. The ring 92 has a hollow interior bore 94 that extends through the ring 92. The rod 12 extends through the ring bore 94. The ring 92 is movable on the rod 12 toward the rod proximal end 14 to a first position of the ring 92 on the rod 12, and toward the rod distal end 16 to a second position of the ring 92 on the rod 12. The ring 92 has a cylindrical base 96 at the ring proximal end. The ring 92 also has a generally conical portion 98 on the distal end of the ring 92. The generally conical portion 98 of the ring 92 has an exterior sliding surface 102. In the preferred embodiment, the sliding surface 102 has a conical configuration. In other embodiments the surface 102 could have more of a convex configuration or more of a concave configuration. The sliding surface 102 on the ring 92 also has a first hardness. In the preferred embodiment, the sliding surface 102 on the ring 92 is an exterior surface of the ring itself. In alternate embodiments, the sliding surface 102 on the ring 92 could be a separate component part secured to the generally conical portion 98 of the ring. For example, the sliding surface 102 could be a stainless steel cap or a Teflon surface secured to or applied to the generally conical portion 98 of the ring 92. In further embodiments, the entire ring 92 could be constructed of stainless steel or a material of similar hardness and having a similar coefficient of friction. A bar 104 extends radially inwardly from the ring conical portion 98 into the ring interior bore 94. The bar 104 extends into the slot 24 on the rod 12 and thereby prevents the ring 92 from rotating on the rod 12 as the ring 92 reciprocates over the rod 12. A tube hole 106 extends through the bar 104. The tube hole has a center axis that is coaxial with the rod center axis 18.

The tube proximal end 54 is press fit into the bar tube hole 106 and is securely attached to the bar 104 and the ring 92. When the ring 92 axially reciprocates on the rod 12, the tube 52 axially reciprocates through the rod center bore 32 and the instrument head center bore 38.

A connection collar 112 is screw threaded onto the external screw threading 22 of the rod 12. The connection collar 112 has an interior bore and internal screw threading 114 that mates or threads with the external screw threading 22 on the rod 12. By turning the connection collar 112 on the rod screw threading 22, the axial position of the collar 112 relative to the rod 12 can be adjusted. The collar 112 has a cylindrical exterior surface that is defined by an intermediate portion 116 of the surface between a proximal end portion 118 and a distal end portion 122 of the surface. The intermediate portion 116 of the connection collar exterior surface is necked down and has a circumferential dimension and a diameter dimension that are slightly smaller than the respective circumferential dimensions and diameter dimensions of the proximal end portion 118 and the distal end portion 122 of the connection collar exterior surface.

A locking hub 132 is secured in the connection collar internal screw threading 114 adjacent the rod proximal end 14. The hub 132 has an interior bore 134 that extends completely through the hub 132. The interior bore 134 has a hexagon configuration defined by an interior surface 136 of the locking hub 132 that surrounds the bore 134. The hub 132 is constructed of a semi-rigid material, for example a plastic material that is self-threading into the internal screw threading 114 of a connection collar 112. The hexagon configuration of the hub interior surface 136 allows a tool such as an Allen wrench to be inserted into the locking hub bore 134 to assist in screw threading the hub 132 into the connection collar internal screw threading 114.

The handle of the microsurgical instrument 10 is comprised of a handle rearward portion 142 and a handle forward portion 144. Although the handle of the described embodiment is provided in two parts, in alternate embodiments of the instrument 10, the handle could be a single, monolithic part comprised of the rearward portion 142 and the forward portion 144. Additionally, the handle rearward portion 142 could be removable from the handle forward portion 144 to enable use of the instrument 10 with only the handle forward portion 144 if desired. In a further embodiment the handle could be comprised of only the forward portion 144.

The handle rearward portion 142 has a generally cylindrical length with opposite proximal 146 and distal 148 ends. The exterior surface of the rearward portion has a smooth, curved configuration designed to fit comfortably behind the web of the surgeon's hand between the thumb and forefinger. The handle rearward portion 142 has a circumferential dimension and an exterior diameter dimension at the distal end 148 that gradually increases as the handle rearward portion 142 extends from the distal end 148 toward the proximal end 146. At about the midpoint of the length of the handle rearward portion 142 the circumferential dimension and exterior diameter dimension begin to decrease as the handle rearward portion 142 extends toward the proximal end 146. This provides the handle rearward portion 142 with the comfortably-shaped exterior surface shown in the drawing figures that rests comfortably on the surgeon's hand behind the web between the thumb and forefinger.

The handle rearward portion 142 has an interior bore 152 that extends completely through the rearward portion 142. The interior bore 152 extending from the handle proximal end 146 is defined by a first interior surface 154 having a reduced interior diameter. As the interior bore 152 continues to extend toward the handle distal end 148 from the first interior surface 154, the bore becomes larger and is defined by a second cylindrical interior surface 156 having a much larger interior diameter dimension than the first interior surface 154. This second interior surface 156 extends through the handle to the handle distal end 148.

The handle forward portion 144 also has a generally cylindrical length between a proximal end 162 and a distal end 164 of the handle forward portion 144. A cylindrical interior bore 166 extends completely through the handle forward portion 144. The exterior surface of the handle forward portion 144 has a cylindrical, necked down portion 168 adjacent the proximal end 162. This portion 168 of the exterior surface is dimensioned to be securely press fit into the second interior surface 156 of the handle rearward portion 142 in attaching the handle forward portion 144 to the handle rearward portion 142. As explained earlier, the press fit connection could enable the handle rearward portion 142 to be selectively removable from the handle forward portion 144. Instead of the press-fit connection, other equivalent connections could be employed such as an adhesive connection or a screw-threaded connection. As the exterior surface of the handle forward portion 144 extends from the necked down portion 168 toward the distal end 164, the exterior surface 170 increases in circumferential dimension and exterior diameter dimension to substantially the same as that of the handle rearward portion 142 at the rearward portion distal end 148. This provides for a smooth transition between the exterior surface of the handle rearward portion 142 to the handle forward portion 144. As the exterior surface 170 of the handle forward portion 144 continues to extend toward the distal end 164 of the handle forward portion, the circumferential dimension and exterior diameter dimension of the exterior surface 170 gradually increase and provide the handle forward portion 144 with the smooth and comfortable exterior surface 170 positioned for gripping by the surgeon's fingertips as shown in the drawing figures. A plurality of circumferential serrations 172 are formed in this area of the exterior surface 170 of the handle forward portion 144 to enhance the grip of the surgeon's fingers on the surface. Beyond the serrations 172 the distal end of the handle forward portion 144 is formed with a rounded, convex surface 174 that curves around the distal end 164 from the handle forward portion exterior surface 170 to the handle forward portion interior bore 166.

The interior bore 166 of the handle forward portion 144 is defined by a first cylindrical interior surface 182 that extends through the handle forward portion 144 from the forward portion proximal end 162. At about the mid-point of the length of the handle forward portion 144, the cylindrical interior surface surrounding the interior bore increases to a second cylindrical interior surface 184 having an interior diameter dimension that is larger than the first cylindrical interior surface 182. The second cylindrical interior surface 184 extends through the interior bore of the handle forward portion 144 from the first cylindrical interior surface 182 to the distal end surface 174 of the handle forward portion.

The rod 12 of the instrument is secured in the interior bore of the handle forward portion 144 by the connection collar 112 being press fit into the first cylindrical interior surface 182 of the handle forward portion. This attaches the handle to the rod proximal end. Other equivalent means could be employed in securing the rod 12 in the interior bore of the handle forward portion 144. Additionally, the handle could be on the rod as one monolithic piece with the rod or at least the rod 12 and the handle forward portion 144 could be made as a single monolithic piece. With the rod 12 secured in the interior bore of the handle forward portion 144, the sliding surface 102 of the ring 92 mounted on the rod 12 is positioned radially inside and axially aligned with the distal end surface 174 of the handle forward portion 144.

A plurality of axially extending slots 186 are formed in the handle forward portion 144 at the distal end 148. The axial slots 186 extend along the length of the handle forward portion 144 from the distal end surface 174 toward the proximal end 162 of the handle forward portion 144. Each slot has a slot end 188 that is axially positioned where the handle forward portion first cylindrical interior surface 182 transitions to the second cylindrical interior surface 184. The plurality of axial slots 186 form a plurality of resilient actuator arms 192 that are circumferentially spaced around the second cylindrical interior surface 184 of the handle forward portion interior bore. As seen in the drawing figures, each of the actuator arms 192 formed by the axial slots 186 has a radial width dimension that is smallest at the slot ends 188 or where the first cylindrical interior surface 182 of the handle forward portion interior bore transitions to the second cylindrical interior surface 184. This gives the actuator arms 192 a radially deflecting resilience. The plurality of slots 186 form each of the actuator arms 192 with an interior surface defined by the second cylindrical interior surface 184 of the handle forward portion 144, and an opposite exterior surface of the actuator arm defined by the exterior surface 170 of the handle forward portion 144. In addition, each of the axial slots 186 defines opposite side surfaces of each actuator arm 192. Each of the arm side surfaces have two planar surface portions 194, 196 that are positioned at an angle relative to each other. Radially inner surface portions 194 of each of the actuator arms 192 are substantially parallel to each other. The inner surface portions 194 of each arm 192 intersect or connect with the actuator arm interior surface defined by the second cylindrical interior surface 184 of the handle forward portion 144. The radially outer surface portions 196 of each arm connect with and extend radially outwardly from the inner surface portions 194 and connect with the exterior surface 170 of the handle forward portion 144. As the radial outer surface portions 196 extend radially outwardly from the inner surface portions 194 toward the exterior surface 170, they merge toward each other. This configuration of the radially outer surface portions 196 increases the circumferential width dimension of the axial slots 186 adjacent the exterior surface 170 of the handle forward portion 144. This increase in the circumferential width of the slots 186 adjacent the exterior surface 170 of the handle forward portion 144 prevents the surgeon's fingers from being pinched in the slots 186 between adjacent arms 192 when the arms 192 are pressed inwardly by the surgeon's fingers.

The rounded, generally convex distal end surface 174 of the handle forward portion 144 is formed by the plurality of slots 186 into a plurality of free distal end surfaces on the plurality of actuator arms 192. What is meant by free distal end surfaces is that the arms cantilever from the proximal end 162 of the handle forward position 144 to the free distal end surfaces 174 and there are no operative connections to the free distal end surfaces. In the at rest positions of the arms 192 the distal end surfaces are positioned in a common radial plane with the ring surface 102 and radially outwardly from and surrounding the ring surface 102. When at least some of the arms 192 are pressed inwardly by the surgeon's fingers, the distal end surfaces 174 of the pressed arms engage in sliding engagement with the ring sliding surface 102. In the preferred embodiment of the instrument, the distal end surfaces 174 of the actuator arms 192 are constructed of a material having a hardness that is less than the hardness of the ring sliding surface 102. In this manner, the sliding movement of the actuator arm distal end surfaces 174 over the ring sliding surface 102 will not wear grooves in the ring sliding surface 102. In addition, the distal end surfaces 174 on the actuator arms 192 could be separate surfaces added to the actuator arms 192. However, in the preferred embodiment of the invention, the distal end surfaces 174 of the actuator arms 192 are surfaces of the arms. Furthermore, in other embodiments the distal end surfaces 179 could make point contact with the ring surface 102 to reduce sliding friction, or the end surfaces could have roller bearings or other equivalent structures that contact the ring surface 102.

With the construction of the microsurgical instrument 10 explained above, the instrument 10 can be comfortably held in the surgeon's hand with the reduced diameter intermediate portion of the instrument where the handle rearward portion 142 merges into the handle forward portion 144 positioned on the web of the hand between the thumb and forefinger. With the surgeon's fingertips gripping at least some of the actuator arms 192 of the handle forward portion 144, manually compressing the arms 192 will cause the arm distal end surfaces 174 to contact the ring surface 102 and exert a compressive force on the sliding surface 102 of the ring 92. This will cause the ring 92 to move axially over the rod 12 toward the rod distal end 16 and the second position of the ring 92 on the rod 12. This in turn causes the ring bar 104 to move the microsurgical instrument tube 52 over the microsurgical instrument shaft 62. This movement actuates the microsurgical instrument at the distal ends of the tube 52 and shaft 62. In the example shown in the drawings, the microsurgical instrument is a microsurgical grasper 198. In addition, the movement of the bar 104 compresses the spring 82.

Releasing the manual compressive force on the actuator arms 192 allows the resiliency of the arms 192 to move the arms back to their at rest positions and also releases the force on the ring 92 urging the ring toward the rod distal end 16. This allows the compressed spring 82 to push the ring 92 over the rod 12 toward the rod proximal end 14 and the first position of the ring on the rod. The movement of the ring 92 could also cause the ring surface 102 to push the arms 192 radially outwardly to their at rest positions. This movement of the ring 92 on the rod 12 also causes the tube 52 to move relative to the shaft 62 and thereby opens the microsurgical surfaces of the grasper 198 formed at the end of the tube 52 and shaft 62.

In view of the foregoing, it will be seen that the several advantages of the invention are achieved and attained.

As various modifications could be made in the construction of the surgical instrument of the invention herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A surgical instrument comprising:
a rod having a length with opposite proximal and distal ends, the rod having a center axis that extends along the rod length and defines mutually perpendicular axial and radial directions relative to the surgical instrument;
a ring mounted on the rod for axially reciprocating movement between first and second positions of the ring on the rod, the ring being movable toward the rod proximal end to the first position of the ring on the rod and the ring being movable toward the rod distal end to the second position of the ring on the rod;
a handle on the rod, the handle having a plurality of arms that are circumferentially spaced around the rod with there being axially extending slots between adjacent arms of the plurality of arms, the plurality of arms extending axially from the rod proximal end along the rod to free distal ends of the arms that are radially outward of and surround the ring, each arm having an interior surface that opposes the rod and an opposite exterior surface, each arm having opposite side surfaces that extend radially between the interior and exterior surfaces of the arm, and at least portions of the opposite side surfaces of each arm merge inwardly toward each other as the opposite side surfaces extend radially from the interior surface to the exterior surface of the arm.

2. The surgical instrument of claim 1, further comprising:
the opposite side surfaces of each arm having portions that are substantially parallel to each other as well as the portions that merge toward each other.

3. The surgical instrument of claim 1, further comprising:
the portions of the opposite side surfaces of each arm that merge toward each other connect with the exterior surface of the arm.

4. The surgical instrument of claim 1, further comprising:
the portions of the opposite side surfaces of each arm that merge toward each other are flat surfaces.

5. The surgical instrument of claim 1, further comprising:
each arm of the plurality of arms has serrations across the exterior surface of the arm.

6. The surgical instrument of claim 1, further comprising:
at least some of the free distal ends of the arms engage against the ring while the ring reciprocates on the rod between the first and second positions of the ring on the rod.

7. The surgical instrument of claim 1, further comprising:
the free distal ends of the arms engaging in a sliding engagement with the ring.

8. The surgical instrument of claim 1, further comprising:
each arm of the plurality of arms having a proximal end that is opposite the distal end of the arm and having a radial width dimension that is smallest at the arm proximal end.

9. The surgical instrument of claim 1, further comprising:
the handle having a handle portion that is secured to the rod proximal end, the plurality of arms being monolithic extensions from the handle portion, and the slots between the adjacent arms extending axially from the free distal ends of the arms toward the handle portion but ending short of the handle portion.

10. The surgical instrument of claim 9, further comprising:
the handle portion secured to the rod proximal end being an intermediate portion of the handle, and the handle having a rearward portion that extends from the handle intermediate portion axially away from the rod proximal end.

11. The surgical instrument of claim 1, further comprising:
the handle having a handle portion that is mounted on the rod proximal end, and the plurality of arms extend from the handle portion mounted on the rod proximal end and cantilever over the rod.

12. The surgical instrument of claim 1, further comprising:
a surgical instrument head on the rod distal end, the surgical instrument head having a center bore with a center axis that is coaxial with the rod center axis;
a surgical instrument tube received in the surgical instrument head center bore for axially reciprocating movement of the surgical instrument tube through the center bore, the surgical instrument tube having opposite proximal and distal ends with the proximal end being operatively connected to the ring for reciprocating movement of the surgical instrument tube and the ring relative to the surgical instrument head and the rod.

13. The surgical instrument of claim 12, further comprising:
a surgical instrument shaft extending through the surgical instrument tube, the surgical instrument shaft having opposite proximal and distal ends with the distal end of the surgical instrument shaft projecting from the distal end of the surgical instrument tube and the proximal end of the surgical instrument shaft projecting from the proximal end of the surgical instrument tube and being secured stationary to the rod.

* * * * *